United States Patent [19]

Echert et al.

[11] Patent Number: 4,924,698
[45] Date of Patent: May 15, 1990

[54] METHOD AND APPARATUS FOR REMOTE MONITORING OF OCEANOGRAPHIC CONDITIONS

[76] Inventors: Douglas C. Echert, 15917 SE. Fairwood Blvd., Renton, Wash. 98058; Edward W. Geller, 3750 79th Ave., SE., Mercer Island, Wash. 98040; Dennis J. Hanzlick, 7735 34th Ave., NE., Seattle, Wash. 98115; James H. Morison, 7438 NE. 129th St., Kirkland, Wash. 98034

[21] Appl. No.: 303,165

[22] Filed: Jan. 27, 1989

[51] Int. Cl.⁵ .................. G01W 1/00; B63B 22/00
[52] U.S. Cl. ................................ 73/170 A; 441/33
[58] Field of Search ............ 73/170 A; 374/136, 137; 441/2, 21, 22, 23, 24, 25, 26, 27, 33

[56] References Cited

U.S. PATENT DOCUMENTS

| | | |
|---|---|---|
| 3,280,633 | 10/1966 | Langguth . |
| 3,402,687 | 9/1968 | Tsuji . |
| 3,570,437 | 3/1971 | Davis, Jr. . |
| 3,572,129 | 3/1971 | Walthier et al. . |
| 3,860,983 | 1/1975 | Furth et al. . |
| 3,906,564 | 9/1975 | Thompson et al. . |
| 3,927,562 | 12/1975 | Hickey, Jr. ............... 73/170 A |
| 3,952,349 | 4/1976 | Erath et al. . |
| 4,116,069 | 9/1978 | Lezgintsev et al. . |
| 4,191,049 | 3/1980 | Bowditch et al. ............ 73/170 A |
| 4,202,034 | 5/1980 | Bowditch et al. . |
| 4,202,036 | 5/1980 | Bowditch et al. . |
| 4,215,572 | 8/1980 | Spiess . |
| 4,266,500 | 5/1981 | Jurcy . |
| 4,301,761 | 11/1981 | Fry et al. . |
| 4,336,709 | 6/1982 | Meek . |
| 4,557,697 | 12/1985 | Kontur et al. . |

Primary Examiner—Charles A. Ruehl
Attorney, Agent, or Firm—Don R. Mollick

[57] ABSTRACT

A method and apparatus for measuring profiles of ocean properties. The apparatus includes a stationary surface buoy to which a weight and cable are attached, the sensors traverse the cable by means of a hydrofoil the pitch of which is varied by a pressure activated sensing system. The apparatus is adapted for use under pack ice or ice bergs. The method is that of moving the sensors in a vertical direction along a guide cable beneath a surface buoy. The cable can hang from the pack ice or be buoyed upward from an anchor on the sea floor.

28 Claims, 2 Drawing Sheets

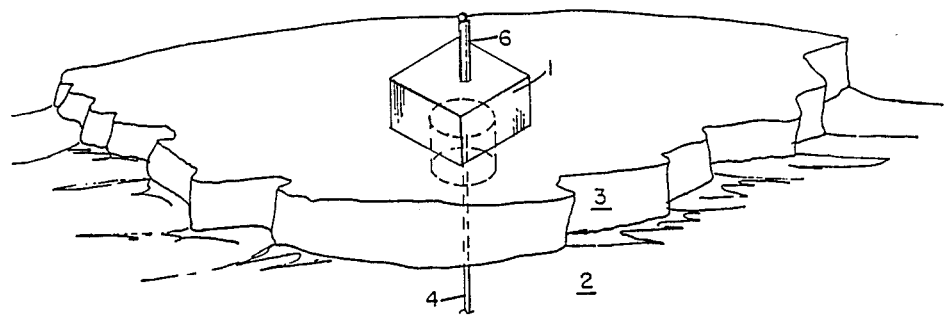
FIG.1
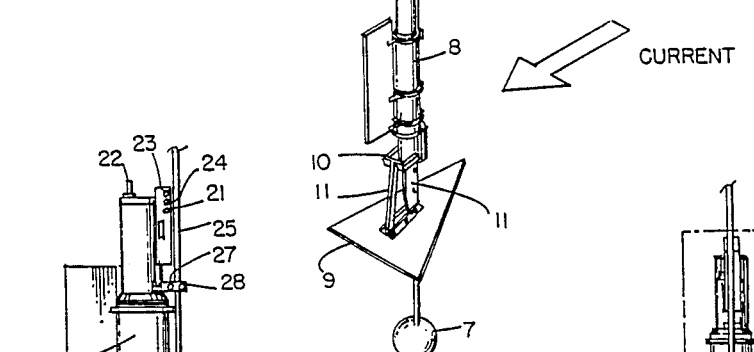
FIG.2
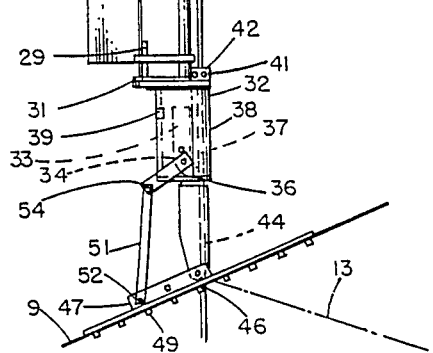
FIG.3
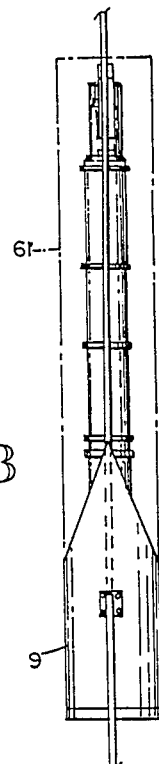

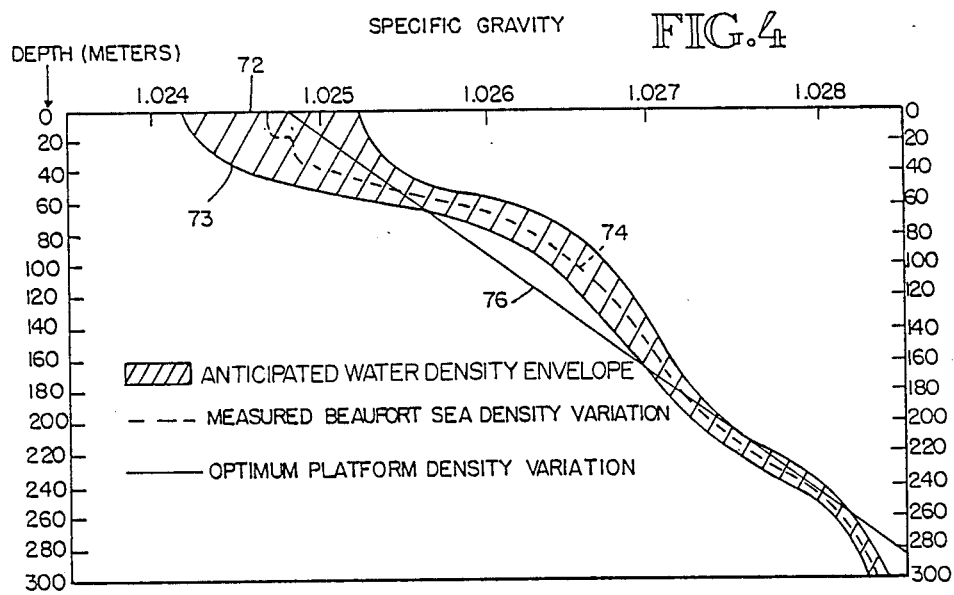
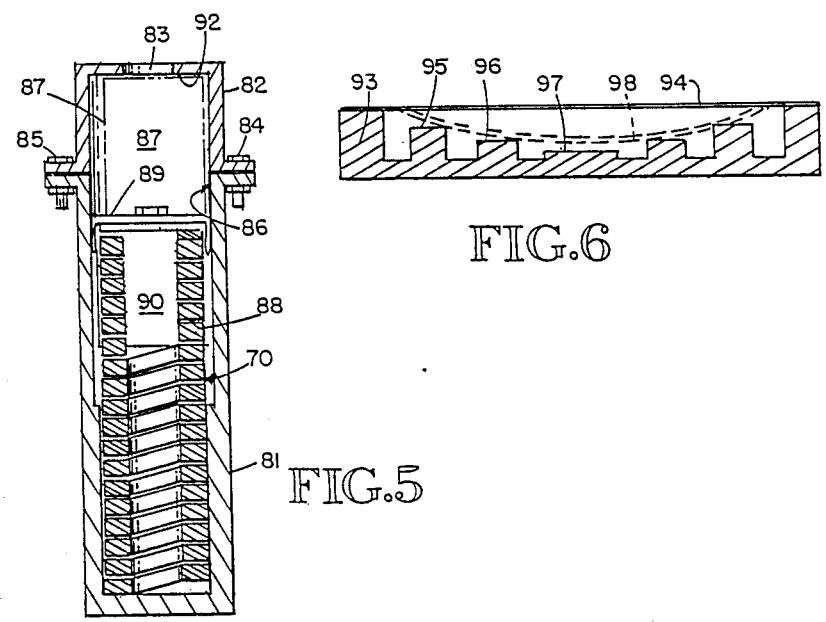

METHOD AND APPARATUS FOR REMOTE MONITORING OF OCEANOGRAPHIC CONDITIONS

FIELD OF THE INVENTION

This invention pertains to remote monitoring of oceanographic conditions. In particular, the invention pertains to remote buoys or sensors for monitoring conditions such as water temperature, salinity, and pressure and then transmitting such data to a remote location. In yet greater particularity, the invention relates to such a remote sensor that is movable in depth.

BACKGROUND OF THE INVENTION

It is often desirable to monitor oceanographic conditions remotely using unattended equipment. The data on such conditions is often useful both for military and civilian purposes. This is particularly true when the area from which the data desired is inhospitable or distant or where the data must be gathered over a long period of time. Such difficult conditions often occur in the arctic and antarctic regions.

A number of methods have been used to remotely monitor oceanographic conditions with automated equipment. The most commonly used arrangement is to moor a cable to an anchor on the seafloor. The cable may be held upright by a surface float(s) or subsurface float(s). On the cable are mounted current meters or devices to measure ocean temperature, conductivity, (for salinity determination), or other variables. These instruments record data internally and the mooring must be recovered from the ocean in order to obtain the data at the end of the experiment. Typically data are not available on a real-time basis during the experiment and if through acts of nature or equipment malfunction, the mooring cannot be recovered, all the data are lost. In ice covered regions such bottom moorings are very difficult to recover. A common innovative technique for experiments has been to hang moorings from the drifting sea ice.

In order to overcome the deficiencies of internally recording instruments it has become a common practice to telemeter data back to shore by HF radio link or via VHF satellite link such as the ARGOS system. This approach is especially useful in ice covered regions when use of a surface buoy makes radio transmission convenient and where recovery to the instruments is often impractical. This technique is described in an article entitled *SALARGOS Temperature-Conductivity Buoys*, published in the September 1982 issue of *Oceans* pp 1255-1260. The telemetry technique can be used in the open ocean if a surface float is used or if a companion surface float is attached to an array of subsurface floats.

The simplest and most common arrangement for the measurements on one of these vertical oceanographic arrays is to attach individual sensors at fixed depths on the cable, even when the data are collected and transmitted to some surface module. The problems with this approach are twofold. In order to measure over a large vertical extent, many sensors must be used and this adds to the cost of the array. Even with a large number of sensors, the vertical resolution of the measurements is limited by the vertical separation between sensors. One way to overcome these cost and resolution problems is somehow to move a single sensor up and down the mooring cable. The technical difficulties with this approach are to provide the power to move the sensor package and, if it is desired to telemeter the data, to transmit data from the moving sensor package to the surface. Providing power to move the sensor package is especially difficult if instrument size is to be constrained and it is desirable to operate the instrument for a long period of time without attention.

Profilers have been proposed that use gas stored at high pressure which is used to control buoyancy in ballast tanks or pump fluid into an external bladder to change buoyancy. Because these devices use stored energy they are too large and too limited in endurance to be practicable for long-term use in ice covered seas. The device described here should achieve long endurance and small size in two ways. First, by not using stored energy but rather by extracting energy for vertical motion from ocean currents. And second, by minimizing the force required for vertical motion by maintaining near neutral buoyancy over a wide range of water depths.

The profiler should not only move a sensor package up and down but also inherently act as a profiling current meter. The device should be suitable in either ice-covered or ice-free seas.

SUMMARY OF THE INVENTION

The invention provides an automatic, unattended instrument system capable of measuring profiles of ocean properties over long periods of time. The system is low cost, thereby permitting the system to be considered expendable for most applications. The system is small and lightweight and can be transported on a deployment aircraft or vessel. The system requires little or no service over its long lifespan. The system provides high vertical resolution, which is unobtainable with individual sensors deployed at fixed depths. The combination of these factors allows ocean investigators to obtain higher quality data at a lower cost than was previously possible.

The apparatus of the invention includes an upper buoy which is fixed to pack ice in the manner of the SALARGOS Temperature-Conductivity Buoy. A cable extends downward through the ice and water. It has one end attached to the buoy and the other end attached to a weight large enough to keep the cable taut. The sensor package is attached to this cable via guides so that it can slide up and down the cable. A wing is attached to the sensor package via a pivot so that it can pitch up and down. Means for altering the pitch of the wing is contained within the sensor package.

In operation the wing is used to "fly" the sensor package up or down the cable. By varying the pitch of the wing a vertical force is applied to the sensor from the currents present in the ocean. This force moves the sensors up or down as desired. The only power required is the small amount needed to vary the wing pitch. The sensor package is thus capable of continuously monitoring various conditions as they change with depth. Only one sensor package is needed and the resolution is only limited by the sensor's resolution.

In addition to serving as a profiling platform for various sensors, the apparatus inherently acts as a current measurement device. The vertical speed of the profiler is a repeatable function of horizontal current speed. It also turns into the direction of the current so, with the addition of a compass to the sensor package, it can be used to measure current direction as well as speed.

It is desireable to minimize the wing size to facilitate handling and deployment. The wing size is determined by the requirement of generating enough lift to counter-act the maximum expected platform weight in water at the minimum operational current speed (i.e., the threshold speed).

Deployment at neutral buoyancy is not possible because of spatial and temporal variations in water density and because of changes in platform density from water absorption. The weight in water is proportional to the displaced volume of the platform and to the deviation of the platform density from the water density. Therefore to minimize the required wing area, it is desireable to minimize the displaced volume of the platform, and to adjust the platform density to the mean of the expected water density during the mission.

Deviations of platform density from water density over the vertical range to be profiled can be minimized by using a pressure/volume compensator to reduce the displaced volume of the platform as it descends into the more dense water. The invention carries a gas-filled spring-loaded bellows to obtain a volume reduction with depth. This same effect can be obtained by a spring-loaded piston or by a gas filled pressure vessel with one or more elastically deformable sides. For compensation that is linear with depth, the maximum density difference between the platform and the ocean is reduced by one half for the ocean density difference shown in FIG. 4. This translates into a fifty percent reduction in wing area.

For any method used, the volume reduction with increasing pressure (depth) can be matched to the water density profile at the particular deployment site. For example, a linear decrease in volume with increasing pressure can be obtained using a spring with a linear spring rate. Non-linear response can be obtained with using a spring with non-linear spring rate, by using multiple springs, or by using a combination of internal gas pressure and spring or springs. The pressure vessel with deformable side(s) can be designed to match the desired decrease in volume with increase in pressure by varying the properties and geometry of the material used for deformable sides.

The size of the wing is also dictated by the design threshold speed. For example, a four fold increase in wing area would be required to obtain a two-fold reduction in this minimum operating current. This minimum will be set by the expected currents at the deployment site.

The resulting apparatus provides a relatively inexpensive lightweight monitor capable of improved resolution.

BRIEF DESCRIPTION OF THE FIGURES

FIG. 1 is a perspective drawing of the apparatus of the invention in a working environment.

FIG. 2 is a side elevation view of the sensor package of the invention.

FIG. 3 is a side elevation view of the sensor package of the invention with the wing in deployment position.

FIG. 4 is a typical density profile of an arctic sea used to determine the wing size of the invention.

FIG. 5 is a section elevation view of the pressure compensator of the invention.

FIG. 6 is a second embodiment of the pressure compensator of the invention.

DETAILED DESCRIPTION OF THE FIGURES

FIG. 1 is a perspective view of the invention in an operating environment. The first portion of the apparatus is a surface buoy 1. The surface buoy 1 is normally situated at the upper surface 2 of the water. If the water is ice covered surface buoy 1 rests on the upper surface of the ice 3. Surface buoy 1 is the residence of the telemetry and signal processing equipment and includes radio transmitters and antennae 6 for transmission of data collected as well as for reception of signals from a base. Attached to and extending downward from surface buoy 1 is a cable 4. A ⅛ inch diameter cable consisting of an insulated copper conductor surrounded by two layers of steel armor has been found suitable for use as cable 4. The armor and inner conductor are electrically connected together at the end of cable 4 near a weight 7. Weight 7 is attached to the end of cable 4 not attached to surface buoy 1. Weight 7 assures that cable 4 is always taut in the deployed position. In the case of deployment on pack ice as shown, a hole must be bored through ice 3 to allow passage of cable 4. An instrument package 8 is slidably attached to cable 4. In this embodiment of the invention attachment of instrument package 8 to cable 4 is by means of two sets of cable roller wheels. Instrument package 8 includes the sensor's batteries and electronics equipment. Instrument package 8 further includes a motor drive. Instrument package 8 may transmit data to surface buoy 1 by inductive linkage through cable 4. A wing 9 is attached to instrument package 8 in a manner to allow rotation perpendicular to cable 4 upon activation of the motor drive in instrument package 8. In this embodiment of the invention attachment of wing 9 to instrument package 8 is by means of a strut 10 and a linkage 11.

In FIG. 1 relative current is indicated by arrow 12. The flow of the water past wing 9 results in hydrodynamic lift. Wing 9 may be constructed from a thin elastic plate such as a sheet of polycarbonate plastic. In the position shown in FIG. 1 the lift exerted on wing 9 by the current urges wing 9 in an upward direction. Since wing 9 is attached to instrument package 8 by strut 10 instrument package 8 will be forced toward the upper surface of the water 2. If wing 9 is rotated into the position shown by the dotted lines 13 instrument package would be forced toward weight 7. Minimal lift force is required to raise or lower instrument package 8 because it is adjusted to have near neutral buoyancy.

The device may be deployed either from a vehicle or the surface of ice 3. In the case of ice deployment a hole must first be bored through ice 3 to enable passage of instrument package 8. First, weight 7 is lowered through the bored hole. Next, linkage 11 is extended to permit wing 9 to rotate to a position parallel to instrument package 8. The flexibility of wing 9 allows it to be rolled about instrument package 8. Wing 9 may be held in this position by use of a deployment tube. The deployment tube containing instrument package 8 and rolled wing 9 is next lowered into the bored hole. Finally, the deployment tube is withdrawn allowing wing 9 to unroll. At the first nose down command, linkage 11 is retracted to its normal operating length and is fixed in position by a detent. If deployment is desired in non-icecovered waters the device may be directly deployed into the water from a sea going vessel or aircraft.

FIG. 2 is a side elevation view of the instrument package of the invention. The sensor package 21 is located at one end 22 of the package. Sensor package 21 includes a conductivity sensor 23, temperature sensor 24 and a pressure sensor 25. Additional sensors could be added if desired.

Attached to sensor package 21 is an electronics package 26. Electronics package 26 includes a microprocessor for directing operation of the invention and signal conditioning means for sensors 23, 24 and 25. A commercial package having these attributes is manufactured by Sea-Bird Electronics, Inc. under the product designation model SBE 19 SEACAT. Electronics package 26 includes a battery to provide power to the system for its lifetime. Attached to the electronics package 26 is an extension wheel bracket 27 including two cable wheels 28. Wheels 28 slidably secure instrument package 8 to cable 4. A weight addition tube 29 is provided at the end 31 of electronics package 26 not attached to sensor pack age 21. Weight addition tube 29 is used to adjust instrument package 8 to near neutral density. A splitter plate 30 is attached to the device. Splitter plate 30 is a vertical fin attached in a position so that it will be down stream of the electronics package 26. The position of electronics package 26 behind cable 4 turns the device into the current. Splitter plate 30 acts to stabilize the device in the current by controlling the shedding of vortices from the cylindrical package.

A drive motor and communications coil housing 32 is also attached to end 31 of electronics package 26. Housing 32 contains a motor 33 for altering the pitch of wing 9. A gear motor having a ratio of 2800:1 providing 400 inch ounces of torque to a 1:1 right angle drive 34 has been found suitable. Motor 33 is electrically linked to electronics package 26 by a cable. A yoke 36 is attached to drive 34 attached to the output of motor 33. Seals 37 are provided at the attachment point of yoke 36 to prevent leakage of sea water into housing 32. Housing 32 further includes a transmission coil 38 to inductively couple data from electronics package 26 to cable 4 allowing telemetry to the surface. Transmission coil 38 is linked to sensor package 21 by the cable passing through electronics package 26. A frequency shift keyed modem in electronics package 26 drives transmission coil 38 which induces a frequency shift keyed signal into cable 4. The inner conductor of cable 4 provides a circuit path for the modem signal and the return path follows the armor to a point near coil 38 where the seawater acts as a shunt around transmitter coil 38. In use, housing 32 is filled with silicone oil to provide lubrication and protection from sea water. A pressure equalizer 39 allows the pressure in housing 32 to adjust to be the same as that of the water where the housing is located, preventing leakage or collapse of the housing. With increasing depth, equalizer 39 also decreases the displaced water volume and therefore counteracts the undesirable increase in buoyancy due to the water density gradient near the surface of the ocean. A second extension wheel bracket 41 and two cable wheels 42 are attached to housing 32. A wing support strut 44 is attached to the end of housing 32 not attached to electronics package 26.

A wing 9 is pivotly attached to the end of wing support strut 44 not attached to housing 32. Attachment is by means of a pin 46 that passes through a hole in strut 44 and holes in two support brackets 47, 48 which in turn are attached to wing 9 by a plurality of fasteners 49. Wing 9 is a flat delta wing. The delta shape provides additional lift over a rectangular wing at low Reynolds numbers and high angles of attack. The delta is also effective at low aspect ratios. These factors allow wing 9 to be smaller in area and much smaller in span than a rectangular wing of similar lift. At the threshold current, the current above which the device is expected to operate, wing 9 must be large enough to generate a lift force that will counteract maximum weight in water, positive or negative. This maximum is the product of the volume of the device and the expected maximum difference in density between the device and the water. A typical value for this maximum density difference is one tenth percent (see the discussion below for FIG. 4), for the volume is 10,000 cubic centimeters, and for the threshold current is 3 centimeters per second. For these conditions a wing area of 2900 square centimeters will provide sufficient lift according to our tests. If through ice deployment is desired, wing 9 should be constructed of a strong flexible material to allow wrapping of wing 9 around housing 32. Polycarbonate plastic has been found to be a suitable material for wing 9. A telescoping linkage 51 is also attached to brackets 47 and 48. The attachment point 52 of linkage 51 is offset from that of pivot pin 46 to provide a torque on wing 9 when linkage 51 is moved. Attachment point 52 includes a pin and holes through brackets 47 and 48 and linkage 51. The telescoping feature of linkage 51 allows furling of wing 9 in the vertical position. A detent holds the telescoping linkage 51 at the appropriate length after the device is first activated. Linkage 51 is attached to yoke 36 at the end 54 opposite pivot 53. End 54 includes a hole for passage of a pin which also passes through both arms of yoke 36.

Pressure sensor 25 controls the operation of the device. A high and low reversal point are preprogrammed into the device. Typical pressures are those corresponding to depths of 10 and 300 meters. When one of these pressure points is reached sensor 25 provides a signal that applies power to motor 33. Motor 33 provides a rotational force to right angle drive 34 when power is applied. The rotation of motor 33 is turned 90 degrees by right angle drive 34. The motion conveyed by drive 34 causes yoke 36 to rotate around the point of location of seals 37. This rotation of yoke 34 in turn pulls linkage 51 in a near vertical direction. Vertical movement of linkage 51 results in a torque on brackets 47 and 48 about pivot pin 46. The result is a rotation of wing 9 about the axis of pin 46. Stops are provided to limit wing 9's rotation to a fixed angle. An angle of ±30 degrees was found to be useful. Wing 9 is continues to rotate until it reaches the opposite pitch stop. When wing 9 is in the opposite pitch, the device slows its ascent or descent and reverses direction. Travel continues in the new direction until the opposite pressure point is attained. Bumpers on cable 4 may be optionally provided to prevent runaway. Once the opposite pressure point is attained the process described above is repeated.

FIG. 3 is a side elevation view of the invention configured for through-ice deployment. All parts are the same as in FIG. 2 except where noted. For through-ice deployment wing 9 is placed in the vertical position. This placement requires that linkage 51 extend into a longer position as shown. Linkage 51 telescopes from a length of 14⅞ inches in the extended position to 10½ inches in the retracted position. Once wing 9 is in the vertical position it is rolled back into the folded configuration shown. The entire sensor package is then placed in a deployment tube 61. Cables or even rubber bands could be substituted for deployment tube 61. It has been found that all components will fit in a 12 inch diameter deployment tube. As described above to deploy through ice a hole of at least 12 inch diameter is first bored through the ice by conventional means. The invention in tube 61 is then inserted in the hole. Once through the ice and into the water, tube 61 is withdrawn allowing wing 9 to unroll into the FIG. 2 position. An initial nose down command is preprogrammed into the microprocessor in sensor package 21. At the first nose down command linkage 51 is shortened into its normal (retracted) operating length and is fixed in position by a detent. Operation is then identical to open water operation as described above. Splitter plate 30 may be dispensed with if a streamlined faring is substituted for the embodiment shown.

FIG. 4 is a typical Arctic Seawater Density Envelope. The vertical scale 71 is the depth in meters and the horizontal scale 72 is the Specific Gravity. The shaded area 73 is the Anticipated Water Density Envelope. The dotted line 74 is the Measured Beaufort Sea Density Variation. Finally the solid line 76 is the optimum linear platform density variation and is the target variation when a buoyancy/volume compensator is used in order to minimize the weight in water positive or negative. A one tenth percent maximum density difference between the water and the platform is indicated by the water density envelope 73 and the platform density line 76.

FIG. 5 is a section side elevation cutaway view of a spring loaded bellows type pressure/volume compensator. A pressure case 81 is provided to house the components. A cap 82 with a hole 83 closes pressure case 81 and is attached by bolts 84, 85. A rolling elastomeric seal 86 is clamped between cap 82 and pressure case 81. The area 87 above seal 86 is vented to the outside environment by hole 83 in cap 82. The area 90 below seal 86 is filled with a gas. A spring 88 is situated in pressure case 81. A spring cap 89 attaches seal 86 to the end of spring 88 not in contact with pressure case 81. In FIG. 5 spring 88 is shown in near maximum compression such as occurs when the pressure of water compresses the gas in area 90 reducing the volume of gas in pressure case 81. If the water pressure is lower the components would tend to assume the position shown by dotted lines 92 where the volume is maximized and the pressure is lower. The linear or non-linear spring characteristics of spring 88 are selected to ensure the volume/pressure change is matched to the water density profile at a particular site to best obtain neutral buoyancy over a depth range. One way to make a non-linear device is to use multiple nested springs of unequal lengths. This increases the stiffness with increasing pressure.

An alternative design for the buoyancy compensator is shown in FIG. 6. It includes a round, metal base plate 93 and a round metal cover plate 94 fastened together in a watertight manner at their edges. Base plate 93 is hollowed out in concentric rings separated by partition/supports 95,96, and 97. The partition/supports 95,96, and 97 are different heights. In the case shown, under the action of water pressure cover plate 94 deflects over its full diameter until it contacts partition/support 95 (the configuration shown by dotted line 98). This stiffens plate 94 during further compression until plate 94 contacts partition/support 96 (the configuration shown by dotted line 99). this results in a further increase in stiffness. Ultimately plate 94 can be forced by water pressure to contact partition/support 97, at which point the compensator is in it's stiffest configuration. The number, height, and arrangement of the partition/supports can be selected to provide the type of nonlinear compressibility which best matches the density profile of the area where the device is to be used. The geometry shown makes it easy to relate the arrangement of the partition/supports 95,96,97 to the resulting non-linear stiffness, because the deflection of round plates under external pressure is well understood.

Obviously many modifications and variations of the present invention are possible in the light of the above teachings. It is therefore to be understood that within the scope of the appended claims the invention may be practiced otherwise than as specifically described.

What is claimed is:

1. An apparatus for remote monitoring of oceanographic conditions comprising:
   a surface buoy for residence on the surface; and,
   a cable attached to said surface buoy suspended downward from said buoy; and,
   a sensor package slidably attached to said cable for sensing oceanographic conditions; and,
   movement means attached to said sensor package for moving said package along said cable in a vertical direction relative to said surface buoy.

2. An apparatus for remote monitoring of oceanographic conditions as in claim 1, wherein said surface buoy rests on the surface of pack ice and ice bergs.

3. An apparatus for remote monitoring of oceanographic conditions as in claim 1, further comprising a weight attached to said cable for maintaining vertical orientation of said cable.

4. An apparatus for remote monitoring of oceanographic conditions as in claim 1, wherein said movement means comprises:
   a wing pivotally attached to said sensor package for providing hydrodynamic lift; and,
   control means attached to said wing for varying its pitch.

5. An apparatus for remote monitoring of oceanographic conditions as in claim 4, wherein said wing is a delta wing.

6. An apparatus for remote monitoring of oceanographic conditions as in claim 4, wherein said wing folds for allowing through-ice deployment in a hole smaller than said wing.

7. An apparatus for remote monitoring of oceanographic conditions as in claim 4, wherein said control means allows said wing to be positioned parallel to said sensor package for deployment.

8. An apparatus for remote monitoring of oceanographic conditions as in claim 4, wherein said control means is activated when a preselected pressure point is attained.

9. An apparatus for remote monitoring of oceanographic conditions as in claim 4, wherein said control means comprises:
   a motor attached to said sensor package for providing rotational force; and,
   a linkage attached to said motor and to said wing; and,
   a pivotal attachment of said wing to said sensor package such that when said motor is activated the pitch of said wing is reversed.

10. An apparatus for remote monitoring of oceanographic conditions as in claim 9, wherein said linkage comprises:
    a yoke attached to said motor for converting rotational motion to vertical motion; and,
    a link attached at one end to said yoke and at the other end to said wing.

11. An apparatus for remote monitoring of oceanographic conditions as in claim 10, wherein said link is retractable for allowing said wing to assume a position parallel to said sensor package.

12. An apparatus for remote monitoring of oceanographic conditions as in claim 1, wherein said sensor package further includes a mechanism for attaining neutral buoyancy.

13. An apparatus for remote monitoring of oceanographic conditions as in claim 12, wherein said means for attaining neutral buoyancy includes an adjustable weight for adjusting the weight of said apparatus to be substantially equal to the weight of water displaced.

14. An apparatus for remote monitoring of oceanographic conditions as in claim 12, wherein said means for attaining neutral buoyancy includes a pressure/volume compensator for reducing the volume of said sensor package as the depth and resulting pressure increases.

15. An apparatus for remote monitoring of oceanographic conditions as in claim 12, wherein said means for attaining neutral buoyancy includes a pressure/volume compensator for reducing the volume of said sensor package as the depth and resulting pressure increases wherein said volume/pressure change is matched to the water density profile at a particular site to best obtain neutral buoyancy over a depth range.

16. An apparatus for remote monitoring of oceanographic conditions as in claim 1, wherein the attachment of said sensor package to said cable is by means of a plurality of guide wheels.

17. An apparatus for remote monitoring of oceanographic conditions as in claim 1, wherein said sensor package further comprises communication means for conveying information to said surface buoy.

18. An apparatus for remote monitoring of oceanographic conditions as in claim 17, wherein said communication means includes a coil for inductive coupling to said cable attached to said surface buoy.

19. An apparatus for remote monitoring of oceanographic conditions as in claim 18, and said coil receives a frequency-shift keyed signal from a modem.

20. An apparatus for remote monitoring of oceanographic conditions as in claim 18, and said cable includes an insulated conductor for use as a signal path, and an armor sheath wherein said insulated conductor is connected to said sheath at one end for use a return path.

21. An apparatus for remote monitoring of oceanographic conditions as in claim 1, wherein said sensor package further includes a battery package for providing electrical power.

22. An apparatus for remote monitoring of oceanographic conditions as in claim 1, wherein said sensor package includes stabilization means for providing stability by controlling and reducing vortices shed by hydrodynamic action.

23. An apparatus for remote monitoring of oceanographic conditions as in claim 22, wherein said stabilization means includes a splitter plate.

24. An apparatus for remote monitoring of oceanographic conditions as in claim 23, wherein said splitter plate is a vertical plate oriented downstream of said sensor package.

25. An apparatus for remote monitoring of oceanographic conditions as in claim 22, wherein said stabilization means is a streamlined fairing.

26. An apparatus for remote monitoring of oceanographic conditions comprising:
 a surface buoy for residence on the surface wherein said surface buoy rests on the surface of pack ice and ice bergs; and,
 a cable attached to said surface buoy extending downward from said buoy; and,
 a sensor package slidably attached to said cable by a plurality of guide wheels for sensing oceanographic conditions wherein said sensor package further includes means for attaining neutral buoyancy including an adjustable weight for adjusting the weight of said apparatus in water, and a pressure compensator for reducing the volume inside of said sensor package as it experiences increasing pressure with increased depth and a coil for inductive coupling to said cable for the relay of data, and a battery package for providing electrical power; and,
 a delta wing pivotally attached to said sensor package for providing hydrodynamic lift wherein said wing folds for allowing through-ice deployment in a hole smaller than said wing; and, control means activated when a preselected pressure point is attained attached to said wing including, a motor attached to said sensor package for providing rotational force, a linkage attached to said motor and to said wing, a pivotal attachment of said wing to said sensor package such that when said motor is activated the pitch of said wing is reversed, a yoke attached to said motor for converting rotational motion to vertical motion, a link attached at one end to said yoke and at the other end to said wing wherein said link is retractable for allowing said wing to assume a position parallel to said sensor package, for varying its pitch attached to said sensor package for moving said package along said cable in a vertical direction relative to said surface buoy wherein said control means allows said wing to be positioned parallel to said sensor package for deployment; and,
 stabilization means attached to said sensor package for providing stability by controlling vortices shed by hydrodynamic action including a vertical splitter plate oriented downstream of said sensor package; and,
 a weight attached to said cable for maintaining vertical orientation of said cable.

27. A method for obtaining a profile of ocean properties comprising the steps of;
 placing a buoy on the surface of the sea in the area in which the profile is sought, and
 suspending a cable from said buoy, and
 moving a sensor in communication with said buoy along said cable through the vertical distance of sea in which data is sought, and
 transmitting the information obtained from said sensor to the place where the data are desired.

28. A method for obtaining a profile of ocean properties as in claim 27, further comprising the steps of;
 boring a hole through ice over the area in which information is sought, and
 inserting said cable and said sensor through the hole.

* * * * *

UNITED STATES PATENT AND TRADEMARK OFFICE
CERTIFICATE OF CORRECTION

PATENT NO. : 4,924,698

DATED : May 15, 1990

INVENTOR(S) : Echert et al

It is certified that error appears in the above-identified patent and that said Letters Patent is hereby corrected as shown below:

Column 1, line 5, insert the following:

--This invention was made with Government support under contract awarded by the Department of the Navy. The Government has certain rights in the invention.--.

Signed and Sealed this

Twenty-eighth Day of July, 1992

Attest:

DOUGLAS B. COMER

*Attesting Officer*   *Acting Commissioner of Patents and Trademarks*